(12) United States Patent
Morton

(10) Patent No.: US 9,048,061 B2
(45) Date of Patent: Jun. 2, 2015

(54) X-RAY SCANNERS AND X-RAY SOURCES THEREFOR

(71) Applicant: Rapiscan Systems, Inc., Torrance, CA (US)

(72) Inventor: Edward James Morton, Guidlford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 14/094,603

(22) Filed: Dec. 2, 2013

(65) Prior Publication Data

US 2014/0161220 A1 Jun. 12, 2014

Related U.S. Application Data

(63) Continuation of application No. 13/086,708, filed on Apr. 14, 2011, now Pat. No. 8,625,735, which is a continuation of application No. 12/485,900, filed on Jun. 16, 2009, now Pat. No. 7,949,101, which is a continuation-in-part of application No. 12/097,422, filed as application No. PCT/GB2006/004684 on Dec. 15, 2006, now Pat. No. 7,876,879.

(30) Foreign Application Priority Data

Dec. 16, 2005 (GB) .................................. 0525593.0
Mar. 12, 2009 (GB) .................................. 0904236.7

(51) Int. Cl.
*H01J 35/02* (2006.01)
*H01J 35/08* (2006.01)
(Continued)

(52) U.S. Cl.
CPC ............ *H01J 35/08* (2013.01); *H01J 2235/088* (2013.01); *G01N 23/06* (2013.01); *G01N 2223/206* (2013.01); *G01V 5/00* (2013.01); *H01J 2235/086* (2013.01); *G01N 23/046* (2013.01)

(58) Field of Classification Search
CPC ........... H01J 35/02; H01J 35/08; H01J 35/24; H01J 35/30; H01J 2235/08; H01J 2235/081; H01J 2235/086; H01J 2235/088
See application file for complete search history.

(56) References Cited

U.S. PATENT DOCUMENTS 2,299,251 A 10/1942 Perbal
2,831,123 A 4/1958 Daly
(Continued)

FOREIGN PATENT DOCUMENTS

AT 392160 B 2/1991
AU 2003254124 A1 2/2004
(Continued)

OTHER PUBLICATIONS

Development of ultra-fast X-ray computed tomography scanner system, INS 98-43 6068772 A9823-8760J:016 (PHA); B98-12-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat. No. 97CH36135), Part No. vol. 2, 1997, pp. 1003-1008 vol. 2, 2 vol. xlviii+1761 page(s), ISBN-0 7803 4258 5.

(Continued)

*Primary Examiner* — Thomas R Artman
(74) *Attorney, Agent, or Firm* — Novel IP

(57) ABSTRACT

The present invention is directed toward an X-ray scanner that has an electron source and an anode. The anode has a target surface with a series of material areas spaced along it in a scanning direction. The material areas are formed from different materials. The electron source is arranged to direct electrons at a series of target areas of the target surface, in a predetermined order, so as to generate X-ray beams having different energy spectra.

19 Claims, 5 Drawing Sheets

(51) Int. Cl.
  *G01N 23/06* (2006.01)
  *G01V 5/00* (2006.01)
  *G01N 23/04* (2006.01)

(56) References Cited

U.S. PATENT DOCUMENTS

| | | |
|---|---|---|
| 2,952,790 A | 9/1960 | Steen |
| 2,999,935 A | 9/1961 | Foster |
| 3,239,706 A | 3/1966 | Farrell |
| 3,707,672 A | 12/1972 | Miller et al. |
| 3,713,156 A | 1/1973 | Pothier |
| 3,766,387 A | 10/1973 | Heffan et al. |
| 3,768,645 A | 10/1973 | Conway |
| 3,784,837 A | 1/1974 | Holmstrom |
| 3,848,130 A | 11/1974 | Macovski |
| 3,854,049 A | 12/1974 | Mistretta et al. |
| RE28,544 E | 9/1975 | Stein et al. |
| 3,965,358 A | 6/1976 | Macovski |
| 3,980,889 A | 9/1976 | Haas |
| 4,047,035 A | 9/1977 | Dennhoven et al. |
| 4,057,725 A | 11/1977 | Wagner |
| 4,105,922 A | 8/1978 | Lambert |
| 4,122,783 A | 10/1978 | Pretini |
| 4,139,771 A | 2/1979 | Dennhoven et al. |
| 4,158,770 A | 6/1979 | Davis, Jr. et al. |
| 4,210,811 A | 7/1980 | Dennhoven et al. |
| 4,216,499 A | 8/1980 | Kunze et al. |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,297,580 A | 10/1981 | Juner |
| 4,340,816 A | 7/1982 | Schott |
| 4,352,021 A | 9/1982 | Boyd |
| 4,366,382 A | 12/1982 | Kotowski |
| 4,375,695 A | 3/1983 | Harding et al. |
| 4,384,209 A | 5/1983 | Wagner et al. |
| 4,399,403 A | 8/1983 | Strandberg, Jr. et al. |
| 4,430,568 A | 2/1984 | Yoshida et al. |
| 4,468,802 A | 8/1984 | Friedel |
| 4,471,343 A | 9/1984 | Lemelson |
| 4,566,113 A | 1/1986 | Donges et al. |
| 4,571,491 A | 2/1986 | Vinegar et al. |
| 4,599,740 A | 7/1986 | Cable |
| 4,622,688 A | 11/1986 | Diemer et al. |
| 4,641,330 A | 2/1987 | Herwig et al. |
| 4,672,649 A | 6/1987 | Rutt |
| 4,675,890 A | 6/1987 | Plessis et al. |
| 4,736,401 A | 4/1988 | Donges et al. |
| 4,754,469 A | 6/1988 | Harding et al. |
| 4,788,704 A | 11/1988 | Donges et al. |
| 4,788,706 A | 11/1988 | Jacobson |
| 4,789,930 A | 12/1988 | Sones et al. |
| 4,825,454 A | 4/1989 | Annis et al. |
| RE32,961 E | 6/1989 | Wagner |
| 4,866,745 A | 9/1989 | Akai |
| 4,868,856 A | 9/1989 | Frith |
| 4,884,289 A | 11/1989 | Glockmann et al. |
| 4,887,604 A | 12/1989 | Shefer et al. |
| 4,956,856 A | 9/1990 | Harding |
| 4,958,363 A * | 9/1990 | Nelson et al. .................. 378/85 |
| 4,975,968 A | 12/1990 | Yukl |
| 4,979,202 A | 12/1990 | Siczek et al. |
| 4,987,584 A | 1/1991 | Doenges |
| 4,991,189 A | 2/1991 | Boomgaarden et al. |
| 5,007,072 A | 4/1991 | Jenkins et al. |
| 5,008,911 A | 4/1991 | Harding |
| 5,022,062 A | 6/1991 | Annis |
| 5,033,106 A | 7/1991 | Kita |
| 5,056,124 A | 10/1991 | Kakimoto et al. |
| 5,065,418 A | 11/1991 | Bermbach et al. |
| 5,081,456 A | 1/1992 | Michiguchi et al. |
| 5,091,924 A | 2/1992 | Bermbach et al. |
| 5,098,640 A | 3/1992 | Gozani et al. |
| 5,105,452 A | 4/1992 | McInerney |
| 5,144,191 A | 9/1992 | Jones et al. |
| 5,172,401 A | 12/1992 | Asari |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,227,800 A | 7/1993 | Huguenin et al. |
| 5,237,598 A | 8/1993 | Albert |
| 5,247,556 A | 9/1993 | Eckert et al. |
| 5,247,561 A | 9/1993 | Kotowski |
| 5,253,283 A | 10/1993 | Annis et al. |
| 5,259,014 A | 11/1993 | Brettschneider |
| 5,263,075 A | 11/1993 | McGann et al. |
| 5,265,144 A | 11/1993 | Harding et al. |
| 5,272,627 A | 12/1993 | Maschhoff |
| 5,313,511 A | 5/1994 | Annis |
| 5,319,547 A | 6/1994 | Krug |
| 5,339,080 A | 8/1994 | Steinway et al. |
| 5,345,240 A | 9/1994 | Frazier |
| 5,365,567 A | 11/1994 | Ohtsuchi et al. |
| 5,367,552 A | 11/1994 | Peschmann |
| 5,379,334 A | 1/1995 | Zimmer et al. |
| 5,410,156 A | 4/1995 | Miller |
| 5,412,702 A | 5/1995 | Sata |
| 5,420,905 A | 5/1995 | Bertozzi |
| 5,467,377 A | 11/1995 | Dawson |
| 5,481,584 A | 1/1996 | Tang et al. |
| 5,490,196 A | 2/1996 | Rudich |
| 5,490,218 A | 2/1996 | Krug |
| 5,493,596 A | 2/1996 | Annis |
| 5,511,104 A | 4/1996 | Mueller et al. |
| 5,524,133 A | 6/1996 | Neale et al. |
| 5,552,705 A | 9/1996 | Keller |
| 5,557,108 A | 9/1996 | Tumer |
| 5,557,283 A | 9/1996 | Sheen et al. |
| 5,570,403 A | 10/1996 | Yamazaki et al. |
| 5,600,303 A | 2/1997 | Husseiny et al. |
| 5,600,700 A | 2/1997 | Krug |
| 5,604,778 A | 2/1997 | Polacin et al. |
| 5,606,167 A | 2/1997 | Miller |
| 5,633,907 A | 5/1997 | Gravelle et al. |
| 5,638,420 A | 6/1997 | Armistead |
| 5,642,393 A | 6/1997 | Krug |
| 5,642,394 A | 6/1997 | Rothschild |
| 5,648,997 A | 7/1997 | Chao |
| 5,651,047 A | 7/1997 | Moorman |
| 5,661,774 A | 8/1997 | Gordon |
| 5,666,393 A | 9/1997 | Annis |
| 5,687,210 A | 11/1997 | Maitrejean et al. |
| 5,689,239 A | 11/1997 | Turner et al. |
| 5,689,541 A | 11/1997 | Schardt |
| 5,692,028 A | 11/1997 | Geus et al. |
| 5,712,926 A | 1/1998 | Eberhard |
| 5,745,543 A | 4/1998 | De Bokx et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,796,802 A | 8/1998 | Gordon |
| 5,805,660 A | 9/1998 | Perion et al. |
| 5,812,630 A | 9/1998 | Blaffert |
| 5,818,897 A | 10/1998 | Gordon |
| 5,838,758 A | 11/1998 | Krug |
| 5,838,759 A | 11/1998 | Armistead |
| 5,841,831 A | 11/1998 | Hell et al. |
| 5,859,891 A | 1/1999 | Hibbard |
| 5,881,122 A | 3/1999 | Crawford |
| 5,887,047 A | 3/1999 | Bailey |
| 5,901,198 A | 5/1999 | Crawford |
| 5,903,623 A | 5/1999 | Swift et al. |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang et al. |
| 5,943,388 A | 8/1999 | Tumer |
| 5,966,422 A | 10/1999 | Dafni et al. |
| 5,974,111 A | 10/1999 | Krug |
| 5,982,843 A | 11/1999 | Bailey |

(56) References Cited

U.S. PATENT DOCUMENTS

| | | |
|---|---|---|
| 5,987,097 A | 11/1999 | Salasoo |
| 6,018,562 A | 1/2000 | Willson |
| 6,021,174 A | 2/2000 | Campbell |
| 6,026,135 A | 2/2000 | McFee et al. |
| 6,026,143 A | 2/2000 | Simanovsky |
| 6,026,171 A | 2/2000 | Hiraoglu |
| 6,031,890 A | 2/2000 | Bermbach et al. |
| 6,035,014 A | 3/2000 | Hiraoglu |
| 6,037,597 A | 3/2000 | Karavolos |
| 6,054,712 A | 4/2000 | Komardin et al. |
| 6,058,158 A | 5/2000 | Eiler |
| 6,067,344 A | 5/2000 | Grodzins et al. |
| 6,067,366 A | 5/2000 | Simanovsky |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins et al. |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo et al. |
| 6,118,852 A | 9/2000 | Rogers |
| 6,122,343 A | 9/2000 | Pidcock |
| 6,125,167 A | 9/2000 | Morgan |
| 6,128,365 A | 10/2000 | Bechwati |
| 6,149,592 A | 11/2000 | Yanof et al. |
| 6,151,381 A | 11/2000 | Grodzins et al. |
| 6,163,591 A | 12/2000 | Benjamin |
| 6,181,765 B1 | 1/2001 | Sribar |
| 6,183,139 B1 | 2/2001 | Solomon |
| 6,184,841 B1 | 2/2001 | Shober et al. |
| 6,185,272 B1 | 2/2001 | Hiraoglu |
| 6,188,743 B1 | 2/2001 | Tybinkowski et al. |
| 6,188,745 B1 | 2/2001 | Gordon |
| 6,188,747 B1 | 2/2001 | Geus et al. |
| 6,192,101 B1 | 2/2001 | Grodzins |
| 6,192,104 B1 | 2/2001 | Adams et al. |
| 6,195,413 B1 | 2/2001 | Geus et al. |
| 6,195,444 B1 | 2/2001 | Simanovsky |
| 6,198,795 B1 | 3/2001 | Naumann et al. |
| 6,216,540 B1 | 4/2001 | Nelson |
| 6,218,943 B1 | 4/2001 | Ellenbogen |
| 6,236,709 B1 | 5/2001 | Perry |
| 6,249,567 B1 | 6/2001 | Rothschild et al. |
| 6,252,929 B1 | 6/2001 | Swift |
| 6,252,932 B1 | 6/2001 | Arakawa |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis et al. |
| 6,282,260 B1 | 8/2001 | Grodzins |
| 6,288,676 B1 | 9/2001 | Maloney |
| 6,292,533 B1 | 9/2001 | Swift |
| 6,301,326 B2 | 10/2001 | Bjorkholm |
| 6,304,629 B1 | 10/2001 | Conway |
| 6,317,509 B1 | 11/2001 | Simanovsky |
| 6,320,933 B1 | 11/2001 | Grodzins et al. |
| 6,324,249 B1 | 11/2001 | Fazzio |
| 6,342,696 B1 | 1/2002 | Chadwick |
| 6,345,113 B1 | 2/2002 | Crawford |
| 6,347,132 B1 | 2/2002 | Annis |
| 6,356,620 B1 | 3/2002 | Rothschild et al. |
| 6,359,582 B1 | 3/2002 | MacAleese et al. |
| 6,417,797 B1 | 7/2002 | Cousins et al. |
| 6,418,189 B1 | 7/2002 | Schafer |
| 6,424,695 B1 | 7/2002 | Grodzins et al. |
| 6,429,578 B1 | 8/2002 | Danielsson |
| 6,430,255 B2 | 8/2002 | Fenkart |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank |
| 6,453,003 B1 | 9/2002 | Springer et al. |
| 6,453,007 B2 | 9/2002 | Adams et al. |
| 6,456,093 B1 | 9/2002 | Merkel et al. |
| 6,456,684 B1 | 9/2002 | Mun et al. |
| 6,459,755 B1 | 10/2002 | Li |
| 6,459,761 B1 | 10/2002 | Grodzins et al. |
| 6,459,764 B1 | 10/2002 | Chalmers |
| 6,469,624 B1 | 10/2002 | Whan et al. |
| 6,473,487 B1 | 10/2002 | Le |
| RE37,899 E | 11/2002 | Grodzins et al. |
| 6,480,141 B1 | 11/2002 | Toth et al. |
| 6,483,894 B2 | 11/2002 | Hartick et al. |
| 6,501,414 B2 | 12/2002 | Arndt et al. |
| 6,507,025 B1 | 1/2003 | Verbinski |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,556,653 B2 | 4/2003 | Hussein |
| 6,563,903 B2 | 5/2003 | Kang et al. |
| 6,563,906 B2 | 5/2003 | Hussein |
| 6,580,778 B2 | 6/2003 | Meder |
| 6,584,170 B2 | 6/2003 | Aust et al. |
| 6,590,956 B2 | 7/2003 | Fenkart et al. |
| 6,597,760 B2 | 7/2003 | Beneke et al. |
| 6,606,516 B2 | 8/2003 | Levine |
| 6,618,466 B1 | 9/2003 | Ning |
| 6,628,745 B1 | 9/2003 | Annis et al. |
| 6,636,581 B2 | 10/2003 | Sorenson |
| 6,647,091 B2 | 11/2003 | Fenkart et al. |
| 6,647,094 B2 | 11/2003 | Harding et al. |
| 6,647,095 B2 | 11/2003 | Hsieh |
| 6,650,276 B2 | 11/2003 | Lawless |
| 6,653,588 B1 | 11/2003 | Gillard-Hickman |
| 6,658,087 B2 | 12/2003 | Chalmers et al. |
| 6,661,866 B1 | 12/2003 | Limkeman et al. |
| 6,663,280 B2 | 12/2003 | Doenges |
| 6,665,373 B1 | 12/2003 | Kotowski et al. |
| 6,665,433 B2 | 12/2003 | Roder |
| 6,687,333 B2 | 2/2004 | Carroll et al. |
| 6,690,766 B2 | 2/2004 | Kresse |
| 6,707,879 B2 | 3/2004 | McClelland et al. |
| 6,715,533 B2 | 4/2004 | Kresse |
| 6,721,387 B1 | 4/2004 | Naidu et al. |
| 6,735,271 B1 | 5/2004 | Rand et al. |
| 6,737,652 B2 | 5/2004 | Lanza et al. |
| 6,748,043 B1 | 6/2004 | Dobbs |
| 6,754,298 B2 | 6/2004 | Fessler |
| 6,760,407 B2 | 7/2004 | Price et al. |
| 6,763,635 B1 | 7/2004 | Lowman |
| 6,768,317 B2 | 7/2004 | Möller et al. |
| 6,770,884 B2 | 8/2004 | Bryman |
| 6,775,348 B2 | 8/2004 | Hoffman |
| 6,785,357 B2 | 8/2004 | Bernardi et al. |
| 6,785,359 B2 | 8/2004 | Lemaitre |
| 6,788,761 B2 | 9/2004 | Bijjani et al. |
| 6,798,863 B2 | 9/2004 | Sato |
| 6,807,248 B2 | 10/2004 | Mihara |
| 6,812,426 B1 | 11/2004 | Kotowski et al. |
| 6,813,374 B1 | 11/2004 | Karimi et al. |
| 6,816,571 B2 | 11/2004 | Bijjani et al. |
| 6,827,265 B2 | 12/2004 | Knowles et al. |
| 6,830,185 B2 | 12/2004 | Tsikos et al. |
| 6,831,590 B1 | 12/2004 | Steinway et al. |
| 6,837,422 B1 | 1/2005 | Meder |
| 6,837,432 B2 | 1/2005 | Tsikos |
| 6,839,403 B1 | 1/2005 | Kotowski et al. |
| 6,843,599 B2 | 1/2005 | Le et al. |
| 6,856,271 B1 | 2/2005 | Hausner |
| 6,856,667 B2 | 2/2005 | Ellengogen |
| 6,859,514 B2 | 2/2005 | Hoffman |
| 6,876,322 B2 | 4/2005 | Keller |
| 6,891,381 B2 | 5/2005 | Bailey et al. |
| 6,894,636 B2 | 5/2005 | Anderton et al. |
| 6,901,135 B2 | 5/2005 | Fox |
| 6,906,329 B2 | 6/2005 | Bryman |
| 6,907,101 B2 | 6/2005 | Hoffman |

(56) References Cited

U.S. PATENT DOCUMENTS

| | | | |
|---|---|---|---|
| 6,920,196 B2 | 7/2005 | Ueno et al. |
| 6,920,197 B2 | 7/2005 | Kang et al. |
| 6,922,455 B2 | 7/2005 | Jurczyk et al. |
| 6,922,460 B2 | 7/2005 | Skatter et al. |
| 6,922,461 B2 | 7/2005 | Kang et al. |
| 6,928,141 B2 | 8/2005 | Carver et al. |
| 6,933,504 B2 | 8/2005 | Hoffman et al. |
| 6,934,354 B2 | 8/2005 | Hoffman |
| 6,940,071 B2 | 9/2005 | Ramsden et al. |
| 6,944,264 B2 | 9/2005 | Bijjani et al. |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey et al. |
| 6,953,935 B1 | 10/2005 | Hoffman |
| 6,957,913 B2 | 10/2005 | Renkart et al. |
| 6,962,289 B2 | 11/2005 | Vatan et al. |
| 6,968,030 B2 | 11/2005 | Hoffman |
| 6,968,034 B2 | 11/2005 | Ellengogen |
| 6,971,577 B2 | 12/2005 | Tsikos et al. |
| 6,973,158 B2 | 12/2005 | Besson |
| 6,975,698 B2 | 12/2005 | Katcha et al. |
| 6,975,703 B2 | 12/2005 | Wilson |
| 6,978,936 B2 | 12/2005 | Tsikos et al. |
| 6,980,627 B2 | 12/2005 | Qiu et al. |
| 6,990,171 B2 | 1/2006 | Toth et al. |
| 6,990,172 B2 | 1/2006 | Toth |
| 6,991,371 B2 | 1/2006 | Georgeson et al. |
| 6,993,115 B2 | 1/2006 | McGuire et al. |
| 6,996,209 B2 | 2/2006 | Marek |
| 7,010,083 B2 | 3/2006 | Hoffman |
| 7,012,256 B1 | 3/2006 | Roos et al. |
| 7,012,989 B2 | 3/2006 | Holland et al. |
| 7,016,459 B2 | 3/2006 | Ellenbogen et al. |
| 7,020,241 B2 | 3/2006 | Beneke et al. |
| 7,020,242 B2 | 3/2006 | Ellenbogen |
| 7,023,950 B1 | 4/2006 | Annis |
| 7,023,956 B2 | 4/2006 | Heaton et al. |
| 7,023,957 B2 | 4/2006 | Bijjani et al. |
| 7,027,553 B2 | 4/2006 | Dunham et al. |
| 7,027,554 B2 | 4/2006 | Gaultier et al. |
| 7,031,430 B2 | 4/2006 | Kaucic, Jr. et al. |
| 7,031,434 B1 | 4/2006 | Saunders et al. |
| 7,034,313 B2 | 4/2006 | Hoffman |
| 7,039,154 B1 | 5/2006 | Ellenbogen et al. |
| 7,039,159 B2 | 5/2006 | Muenchau et al. |
| 7,045,787 B1 | 5/2006 | Verbinski et al. |
| 7,046,756 B2 | 5/2006 | Hoffman |
| 7,046,761 B2 | 5/2006 | Ellenbogen et al. |
| 7,050,529 B2 | 5/2006 | Hoffman |
| 7,050,536 B1 | 5/2006 | Fenkart et al. |
| 7,050,540 B2 * | 5/2006 | Wilkins et al. ............... 378/124 |
| 7,054,408 B2 | 5/2006 | Jiang et al. |
| 7,062,009 B2 | 6/2006 | Karimi et al. |
| 7,062,011 B1 | 6/2006 | Tybinkowski et al. |
| 7,062,074 B1 | 6/2006 | Beneke |
| 7,064,334 B2 | 6/2006 | Hoffman et al. |
| 7,065,175 B2 | 6/2006 | Green |
| 7,065,179 B2 | 6/2006 | Block et al. |
| 7,068,749 B2 | 6/2006 | Kollegal et al. |
| 7,068,750 B2 | 6/2006 | Toth et al. |
| 7,068,751 B2 | 6/2006 | Toth et al. |
| 7,072,434 B1 | 7/2006 | Tybinkowski et al. |
| 7,076,029 B2 | 7/2006 | Toth et al. |
| 7,078,699 B2 | 7/2006 | Seppi |
| 7,081,628 B2 | 7/2006 | Granfors et al. |
| 7,084,404 B2 | 8/2006 | Hoffman et al. |
| 7,087,902 B2 | 8/2006 | Wang et al. |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,103,137 B2 | 9/2006 | Seppi et al. |
| 7,110,488 B2 | 9/2006 | Katcha et al. |
| 7,112,797 B2 | 9/2006 | Hoge |
| 7,116,749 B2 | 10/2006 | Besson |
| 7,116,751 B2 | 10/2006 | Ellenbogen et al. |
| 7,119,553 B2 | 10/2006 | Yang et al. |
| 7,120,222 B2 | 10/2006 | Hoffman |
| 7,123,681 B2 | 10/2006 | Ellenbogen et al. |
| 7,127,027 B2 | 10/2006 | Hoffman |
| 7,130,374 B1 | 10/2006 | Jacobs et al. |
| 7,133,491 B2 | 11/2006 | Bernardi et al. |
| 7,136,450 B2 | 11/2006 | Ying et al. |
| 7,136,451 B2 | 11/2006 | Naidu et al. |
| 7,139,367 B1 | 11/2006 | Le |
| 7,139,406 B2 | 11/2006 | McClelland et al. |
| 7,142,629 B2 | 11/2006 | Edic et al. |
| 7,149,278 B2 | 12/2006 | Arenson et al. |
| 7,149,339 B2 | 12/2006 | Veneruso |
| 7,155,812 B1 | 1/2007 | Peterson et al. |
| 7,158,611 B2 | 1/2007 | Heismann et al. |
| 7,164,747 B2 | 1/2007 | Ellenbogen et al. |
| 7,164,750 B2 | 1/2007 | Nabors et al. |
| 7,166,458 B2 | 1/2007 | Ballerstadt et al. |
| 7,167,539 B1 | 1/2007 | Hoffman |
| 7,173,998 B2 | 2/2007 | Hoffman et al. |
| 7,177,387 B2 | 2/2007 | Yasunaga et al. |
| 7,177,391 B2 | 2/2007 | Chapin et al. |
| 7,183,906 B2 | 2/2007 | Zanovitch et al. |
| 7,187,756 B2 | 3/2007 | Gohno et al. |
| 7,190,757 B2 | 3/2007 | Ying et al. |
| 7,192,031 B2 | 3/2007 | Dunham et al. |
| 7,197,113 B1 | 3/2007 | Katcha et al. |
| 7,197,116 B2 | 3/2007 | Dunham |
| 7,197,172 B1 | 3/2007 | Naidu et al. |
| 7,203,269 B2 | 4/2007 | Huber |
| 7,203,271 B2 | 4/2007 | Benz et al. |
| 7,203,629 B2 | 4/2007 | Naidu |
| 7,206,379 B2 | 4/2007 | Lemaitre |
| 7,207,713 B2 | 4/2007 | Lowman |
| 7,215,731 B1 | 5/2007 | Basu et al. |
| 7,215,738 B2 | 5/2007 | Muenchau et al. |
| 7,218,700 B2 | 5/2007 | Huber et al. |
| 7,218,704 B1 | 5/2007 | Adams et al. |
| 7,224,763 B2 | 5/2007 | Naidu et al. |
| 7,224,765 B2 | 5/2007 | Ellenbogen |
| 7,224,766 B2 | 5/2007 | Jiang et al. |
| 7,224,769 B2 | 5/2007 | Turner |
| 7,233,640 B2 | 6/2007 | Ikhlef et al. |
| 7,233,644 B1 | 6/2007 | Bendahan et al. |
| 7,236,564 B2 | 6/2007 | Hopkins et al. |
| 7,238,945 B2 | 7/2007 | Hoffman et al. |
| 7,247,856 B2 | 7/2007 | Hoge |
| 7,251,310 B2 | 7/2007 | Smith |
| 7,260,170 B2 | 8/2007 | Arenson et al. |
| 7,260,171 B1 | 8/2007 | Arenson et al. |
| 7,260,172 B2 | 8/2007 | Arenson et al. |
| 7,260,173 B2 | 8/2007 | Wakayama et al. |
| 7,260,174 B2 | 8/2007 | Hoffman et al. |
| 7,260,182 B2 | 8/2007 | Toth et al. |
| 7,263,160 B2 | 8/2007 | Schlomka et al. |
| 7,266,180 B1 | 9/2007 | Saunders et al. |
| 7,272,429 B2 | 9/2007 | Walker et al. |
| 7,274,767 B2 | 9/2007 | Clayton et al. |
| 7,277,577 B2 | 10/2007 | Ying et al. |
| 7,279,120 B2 | 10/2007 | Cheng et al. |
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin et al. |
| 7,295,019 B2 | 11/2007 | Yang et al. |
| 7,295,651 B2 | 11/2007 | Delgado et al. |
| 7,298,812 B2 | 11/2007 | Tkaczyk et al. |
| 7,302,083 B2 | 11/2007 | Larson et al. |
| 7,308,073 B2 | 12/2007 | Tkaczyk et al. |
| 7,308,074 B2 | 12/2007 | Jiang et al. |
| 7,308,077 B2 | 12/2007 | Bijjani et al. |
| 7,317,195 B2 | 1/2008 | Eikman |
| 7,317,390 B2 | 1/2008 | Huey et al. |
| 7,319,737 B2 | 1/2008 | Singh |
| 7,322,745 B2 | 1/2008 | Agrawal et al. |
| 7,324,625 B2 | 1/2008 | Eilbert |
| 7,327,853 B2 | 2/2008 | Ying et al. |

(56) References Cited

U.S. PATENT DOCUMENTS

| | | |
|---|---|---|
| 7,330,527 B2 | 2/2008 | Hoffman et al. |
| 7,330,535 B2 | 2/2008 | Arenson et al. |
| 7,333,587 B2 | 2/2008 | De Man et al. |
| 7,333,588 B2 | 2/2008 | Mistretta et al. |
| 7,333,589 B2 | 2/2008 | Ellenbogen et al. |
| 7,335,887 B1 | 2/2008 | Verbinski et al. |
| 7,336,769 B2 | 2/2008 | Arenson et al. |
| 7,340,525 B1 | 3/2008 | Bhatia et al. |
| 7,349,525 B2 | 3/2008 | Morton et al. |
| 7,369,640 B2 | 5/2008 | Seppi et al. |
| 7,369,643 B2 | 5/2008 | Kotowski et al. |
| 7,372,934 B2 | 5/2008 | De Man et al. |
| 7,400,701 B1 | 7/2008 | Cason |
| 7,440,543 B2 | 10/2008 | Morton |
| 7,486,760 B2 | 2/2009 | Harding |
| 7,486,769 B2 | 2/2009 | Brondo |
| 7,492,855 B2 | 2/2009 | Hopkins et al. |
| 7,505,563 B2 | 3/2009 | Morton et al. |
| 7,512,215 B2 | 3/2009 | Morton et al. |
| 7,564,939 B2 | 7/2009 | Morton et al. |
| 7,579,845 B2 | 8/2009 | Peschmann |
| 7,590,215 B2 | 9/2009 | Schlomka |
| 7,593,506 B2 | 9/2009 | Cason |
| 7,636,638 B2 | 12/2009 | Russ et al. |
| 7,643,866 B2 | 1/2010 | Heismann |
| 7,649,981 B2 | 1/2010 | Seppi et al. |
| 7,664,230 B2 | 2/2010 | Morton et al. |
| 7,684,538 B2 | 3/2010 | Morton et al. |
| 7,724,868 B2 | 5/2010 | Morton |
| 7,734,066 B2 | 6/2010 | DeLia et al. |
| 7,769,132 B1 | 8/2010 | Hurd et al. |
| 7,778,382 B2 | 8/2010 | Hoffman |
| 7,835,495 B2 | 11/2010 | Harding |
| 7,876,879 B2 | 1/2011 | Morton |
| 7,903,789 B2 | 3/2011 | Morton et al. |
| 7,929,663 B2 | 4/2011 | Morton |
| 7,949,101 B2 | 5/2011 | Morton |
| 8,135,110 B2 | 3/2012 | Morton |
| 8,138,770 B2 | 3/2012 | Peschmann |
| 2001/0022346 A1 | 9/2001 | Katagami et al. |
| 2001/0033635 A1 | 10/2001 | Kuwabara |
| 2001/0050972 A1 | 12/2001 | Yamada |
| 2002/0008655 A1 | 1/2002 | Haj-Yousef |
| 2002/0031202 A1 | 3/2002 | Callerame |
| 2002/0094064 A1 | 7/2002 | Zhou et al. |
| 2002/0094117 A1 | 7/2002 | Funahashi |
| 2002/0097836 A1 | 7/2002 | Grodzins |
| 2002/0101958 A1 | 8/2002 | Bertsche |
| 2002/0176531 A1 | 11/2002 | McClelland |
| 2003/0009202 A1 | 1/2003 | Levine |
| 2003/0021377 A1 | 1/2003 | Turner et al. |
| 2003/0031352 A1 | 2/2003 | Nelson et al. |
| 2003/0048868 A1 | 3/2003 | Bailey et al. |
| 2003/0053597 A1 | 3/2003 | Flohr et al. |
| 2003/0076921 A1 | 4/2003 | Mihara et al. |
| 2003/0076924 A1 | 4/2003 | Mario et al. |
| 2003/0085163 A1 | 5/2003 | Chan et al. |
| 2003/0108155 A1 | 6/2003 | Wilkins et al. |
| 2003/0179126 A1 | 9/2003 | Jablonski et al. |
| 2003/0190011 A1 | 10/2003 | Beneke et al. |
| 2003/0216644 A1 | 11/2003 | Hall |
| 2004/0010127 A1 | 1/2004 | Linder |
| 2004/0017224 A1 | 1/2004 | Tumer et al. |
| 2004/0017888 A1 | 1/2004 | Seppi et al. |
| 2004/0077943 A1 | 4/2004 | Meaney et al. |
| 2004/0081270 A1 | 4/2004 | Heuscher |
| 2004/0096030 A1 | 5/2004 | Banchieri |
| 2004/0101098 A1 | 5/2004 | Bijjani et al. |
| 2004/0120454 A1 | 6/2004 | Ellenbogen et al. |
| 2004/0141584 A1 | 7/2004 | Bernardi et al. |
| 2004/0213378 A1 | 10/2004 | Zhou et al. |
| 2004/0213379 A1 | 10/2004 | Bittl |
| 2004/0223585 A1 | 11/2004 | Heismann et al. |
| 2004/0232054 A1 | 11/2004 | Brown et al. |
| 2004/0245449 A1 | 12/2004 | Nakashige et al. |
| 2004/0252807 A1 | 12/2004 | Skatter |
| 2004/0258198 A1 | 12/2004 | Carver et al. |
| 2004/0258305 A1 | 12/2004 | Burnham |
| 2005/0031075 A1 | 2/2005 | Hopkins |
| 2005/0053189 A1 | 3/2005 | Gohno |
| 2005/0058242 A1 | 3/2005 | Peschmann |
| 2005/0084069 A1 | 4/2005 | Du et al. |
| 2005/0084073 A1 | 4/2005 | Seppi et al. |
| 2005/0089140 A1 | 4/2005 | Mario |
| 2005/0105682 A1 | 5/2005 | Heumann |
| 2005/0111610 A1 | 5/2005 | De Man et al. |
| 2005/0111619 A1 | 5/2005 | Bijjani et al. |
| 2005/0157925 A1 | 7/2005 | Lorenz |
| 2005/0169422 A1 | 8/2005 | Ellenbogen |
| 2005/0169423 A1 | 8/2005 | Ellenbogen et al. |
| 2005/0180542 A1 | 8/2005 | Leue et al. |
| 2005/0190882 A1 | 9/2005 | McGuire |
| 2005/0226364 A1 | 10/2005 | Bernard De Man et al. |
| 2005/0238232 A1 | 10/2005 | Ying et al. |
| 2005/0249416 A1 | 11/2005 | Leue et al. |
| 2005/0281390 A1 | 12/2005 | Bernard |
| 2006/0002585 A1 | 1/2006 | Larson et al. |
| 2006/0008047 A1 | 1/2006 | Zhou |
| 2006/0018428 A1 | 1/2006 | Li et al. |
| 2006/0109949 A1 | 5/2006 | Tkaczyk et al. |
| 2006/0113163 A1 | 6/2006 | Hu et al. |
| 2006/0133571 A1 | 6/2006 | Winsor |
| 2006/0145771 A1 | 7/2006 | Strange |
| 2006/0233295 A1 | 10/2006 | Edic et al. |
| 2006/0273259 A1 | 12/2006 | Li et al. |
| 2006/0280286 A1 | 12/2006 | Kaval |
| 2007/0003003 A1 | 1/2007 | Seppi et al. |
| 2007/0025512 A1 | 2/2007 | Gertsenshteyn et al. |
| 2007/0053495 A1 | 3/2007 | Morton et al. |
| 2007/0096030 A1 | 5/2007 | Li et al. |
| 2007/0110215 A1 | 5/2007 | Li |
| 2007/0122003 A1 | 5/2007 | Dobkin et al. |
| 2007/0133740 A1 | 6/2007 | Kang et al. |
| 2007/0172024 A1 | 7/2007 | Morton et al. |
| 2007/0183568 A1 | 8/2007 | Kang et al. |
| 2007/0189597 A1 | 8/2007 | Limer et al. |
| 2007/0237288 A1 | 10/2007 | Tkaczyk et al. |
| 2007/0242802 A1 | 10/2007 | Dafni |
| 2007/0263767 A1 | 11/2007 | Brondo |
| 2008/0043912 A1 | 2/2008 | Harding |
| 2008/0056432 A1 | 3/2008 | Pack et al. |
| 2008/0056435 A1 | 3/2008 | Basu et al. |
| 2008/0198967 A1 | 8/2008 | Connelly |
| 2008/0237480 A1 | 10/2008 | Robinson |
| 2008/0267355 A1 | 10/2008 | Morton et al. |
| 2009/0003514 A1 | 1/2009 | Edic et al. |
| 2009/0010386 A1 | 1/2009 | Peschmann |
| 2009/0034792 A1 | 2/2009 | Kennison et al. |
| 2009/0161816 A1 | 6/2009 | De Man et al. |
| 2009/0207967 A1 | 8/2009 | Liu et al. |
| 2009/0265386 A1 | 10/2009 | March et al. |
| 2010/0020920 A1 | 1/2010 | Mertelmeier |
| 2010/0020934 A1 | 1/2010 | Morton |
| 2010/0329532 A1 | 12/2010 | Masuda et al. |

FOREIGN PATENT DOCUMENTS

| | | |
|---|---|---|
| CA | 2365045 | 6/2003 |
| CN | 85107860 A | 10/1986 |
| CN | 1050769 | 4/1991 |
| CN | 1130498 A | 9/1996 |
| CN | 1309768 | 8/2001 |
| CN | 1550215 A | 12/2004 |
| CN | 1626039 A | 6/2005 |
| CN | 1708256 A | 12/2005 |
| CN | 1795527 A | 6/2006 |
| CN | 100371689 C | 7/2006 |
| DE | 2729353 A1 | 1/1979 |
| DE | 4410757 A1 | 1/1995 |
| DE | 4436688 A1 | 4/1996 |
| DE | 102004056590 A1 | 6/2005 |
| EP | 2328280 A1 | 5/1977 |
| EP | 0198276 A1 | 10/1986 |
| EP | 0424912 A2 | 5/1991 |

(56) References Cited

FOREIGN PATENT DOCUMENTS

| | | |
|---|---|---|
| EP | 0432568 | 6/1991 |
| EP | 0531993 A1 | 3/1993 |
| EP | 0584871 A1 | 3/1994 |
| EP | 0795919 A2 | 9/1997 |
| EP | 0873511 A1 | 10/1998 |
| EP | 0924742 A2 | 6/1999 |
| EP | 0930046 A2 | 7/1999 |
| EP | 1277439 A1 | 1/2003 |
| EP | 1298055 A2 | 4/2003 |
| EP | 1371970 A2 | 12/2003 |
| EP | 1374776 A1 | 1/2004 |
| EP | 1540318 A1 | 6/2005 |
| EP | 1558142 A1 | 8/2005 |
| EP | 1618584 A2 | 1/2006 |
| EP | 1689640 A2 | 8/2006 |
| GB | 1497396 A | 1/1978 |
| GB | 1526041 A | 9/1978 |
| GB | 2015245 A | 9/1979 |
| GB | 2089109 A | 6/1982 |
| GB | 2133208 | 7/1984 |
| GB | 2212903 A | 8/1989 |
| GB | 2329817 A | 3/1995 |
| GB | 2285506 A | 7/1995 |
| GB | 2299251 | 9/1996 |
| GB | 2356453 A | 5/2001 |
| GB | 2414072 A | 11/2005 |
| GB | 2416655 A | 2/2006 |
| GB | 2416944 A | 2/2006 |
| GB | 2417821 A | 3/2006 |
| GB | 2418529 A | 3/2006 |
| GB | 2423687 A | 8/2006 |
| GB | 2437777 A | 11/2007 |
| GB | 2471421 A | 12/2010 |
| JP | 50012990 | 2/1975 |
| JP | S5427793 | 3/1979 |
| JP | S5717524 A | 1/1982 |
| JP | 570175247 | 10/1982 |
| JP | S57175247 A | 10/1982 |
| JP | 590016254 | 1/1984 |
| JP | S5916254 A | 1/1984 |
| JP | 59075549 | 4/1984 |
| JP | 59174744 | 10/1984 |
| JP | 600015546 | 1/1985 |
| JP | S601554 A | 1/1985 |
| JP | S602144 | 1/1985 |
| JP | 600021440 | 2/1985 |
| JP | 60073442 A | 4/1985 |
| JP | 62064977 | 3/1987 |
| JP | 64034333 A | 2/1989 |
| JP | 05100037 A | 4/1993 |
| JP | 05192327 A | 8/1993 |
| JP | H05060381 | 9/1993 |
| JP | 5325851 | 12/1993 |
| JP | 060038957 | 2/1994 |
| JP | H06169911 | 6/1994 |
| JP | 6296607 | 10/1994 |
| JP | H08299322 | 11/1996 |
| JP | 10005206 A | 1/1998 |
| JP | 10075944 A | 3/1998 |
| JP | 1998075944 A | 3/1998 |
| JP | 10506195 | 6/1998 |
| JP | H10211196 A | 8/1998 |
| JP | 11146871 A | 6/1999 |
| JP | 11262486 A | 9/1999 |
| JP | 2000107173 A | 4/2000 |
| JP | 2001083171 | 3/2001 |
| JP | 2001176408 A | 6/2001 |
| JP | 2001233440 | 8/2001 |
| JP | 2002503816 | 2/2002 |
| JP | 2002162472 | 6/2002 |
| JP | 2002168805 | 6/2002 |
| JP | 2002195961 | 7/2002 |
| JP | 2002320610 A | 11/2002 |
| JP | 2002370814 | 12/2002 |
| JP | 2003126075 A | 5/2003 |
| JP | 2003135442 | 5/2003 |
| JP | 2004000605 A | 1/2004 |
| JP | 2004079128 A | 3/2004 |
| JP | 2004233206 | 8/2004 |
| JP | 2005013768 A | 1/2005 |
| JP | 2005110722 | 4/2005 |
| JP | 2005177469 A | 7/2005 |
| JP | 2005534009 A | 11/2005 |
| JP | 2006071514 | 3/2006 |
| JP | 2006167463 | 6/2006 |
| JP | 2006320464 | 11/2006 |
| JP | 2006524809 A | 11/2006 |
| JP | 2007010455 | 1/2007 |
| JP | 2007500357 A | 1/2007 |
| JP | 2007508561 A | 4/2007 |
| JP | 2007533993 A | 11/2007 |
| JP | 2008212840 | 9/2008 |
| JP | 2009519457 | 5/2009 |
| NL | 1021026 | 1/2004 |
| NL | 1027596 | 5/2005 |
| NL | 1027596 C2 | 11/2005 |
| WO | 9217771 | 3/1992 |
| WO | 9217771 A1 | 10/1992 |
| WO | 9528715 A2 | 10/1995 |
| WO | 9718462 | 5/1997 |
| WO | 9718462 A1 | 5/1997 |
| WO | 9941676 | 8/1999 |
| WO | 9950882 | 10/1999 |
| WO | 9960387 A2 | 11/1999 |
| WO | 0231857 | 4/2002 |
| WO | 0231857 A1 | 4/2002 |
| WO | 02031857 | 4/2002 |
| WO | 03029844 | 4/2003 |
| WO | 03042674 | 5/2003 |
| WO | 03051201 | 6/2003 |
| WO | 03051201 A2 | 6/2003 |
| WO | 03065772 | 8/2003 |
| WO | 03105159 | 12/2003 |
| WO | 2004008968 A1 | 1/2004 |
| WO | 2004008970 A1 | 1/2004 |
| WO | 2004010127 A1 | 1/2004 |
| WO | 2004010381 A1 | 1/2004 |
| WO | 2004031755 | 4/2004 |
| WO | 2004037088 | 5/2004 |
| WO | 2004054329 A2 | 6/2004 |
| WO | 2004096050 | 11/2004 |
| WO | 2004097344 A2 | 11/2004 |
| WO | 2004097386 | 11/2004 |
| WO | 2004097886 A2 | 11/2004 |
| WO | 2004097888 | 11/2004 |
| WO | 2004097888 A2 | 11/2004 |
| WO | 2004097889 A2 | 11/2004 |
| WO | 2010097621 | 11/2004 |
| WO | 2004105610 A | 12/2004 |
| WO | 2004111625 | 12/2004 |
| WO | 2005017566 A2 | 2/2005 |
| WO | 2005050405 A2 | 6/2005 |
| WO | 2005084351 | 9/2005 |
| WO | 2005095931 | 10/2005 |
| WO | 2005102170 | 11/2005 |
| WO | 2006027122 A1 | 3/2006 |
| WO | 2006047718 | 5/2006 |
| WO | 2006135586 | 12/2006 |
| WO | 2006137919 | 12/2006 |
| WO | 2007051418 | 5/2007 |
| WO | 2007068933 | 6/2007 |
| WO | 2007068933 A1 | 6/2007 |
| WO | 2007076707 | 7/2007 |
| WO | 2007079675 | 7/2007 |
| WO | 2008027703 | 3/2008 |
| WO | 2008027703 A2 | 3/2008 |
| WO | 2008094305 | 8/2008 |
| WO | 2009005932 | 1/2009 |
| WO | 2009006044 | 1/2009 |
| WO | 2009025935 | 2/2009 |

(56) References Cited

FOREIGN PATENT DOCUMENTS

| WO | 2010097621 A2 | 9/2010 |
|---|---|---|
| WO | 2010138607 A1 | 12/2010 |
| WO | 20012115629 A1 | 8/2012 |

OTHER PUBLICATIONS

Combined Search and Examination Report for GB1017187.4, CXR Ltd.

Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.

International Search Report for PCT/US11/25777, Jul. 26, 2011, Rapiscan Systems, Inc.
Int'l. Search Report PCT/US2010/36221, Aug. 23, 2010, Rapiscan Security Productions, Inc.
International Search Report PCT/GB2006/004684, May 23, 2007, CXR Limited.
International Search Report PCT/GB2004/001751 Mar. 21, 2005.
International Search Report PCT/GB2004/001732 Feb. 25, 2005.
International Search Report PCT/GB2004/001731 May 27, 2005.
International Search Report PCT/GB2004/001741 Mar. 3, 2005.
International Search Report PCT/GB2004/001747 Aug. 10, 2004.
International Search Report PCT/GB2004/001729 Aug. 12, 2004.
US 5,987,079, 11/1999, Scott (withdrawn)

* cited by examiner

*Fig. 1*
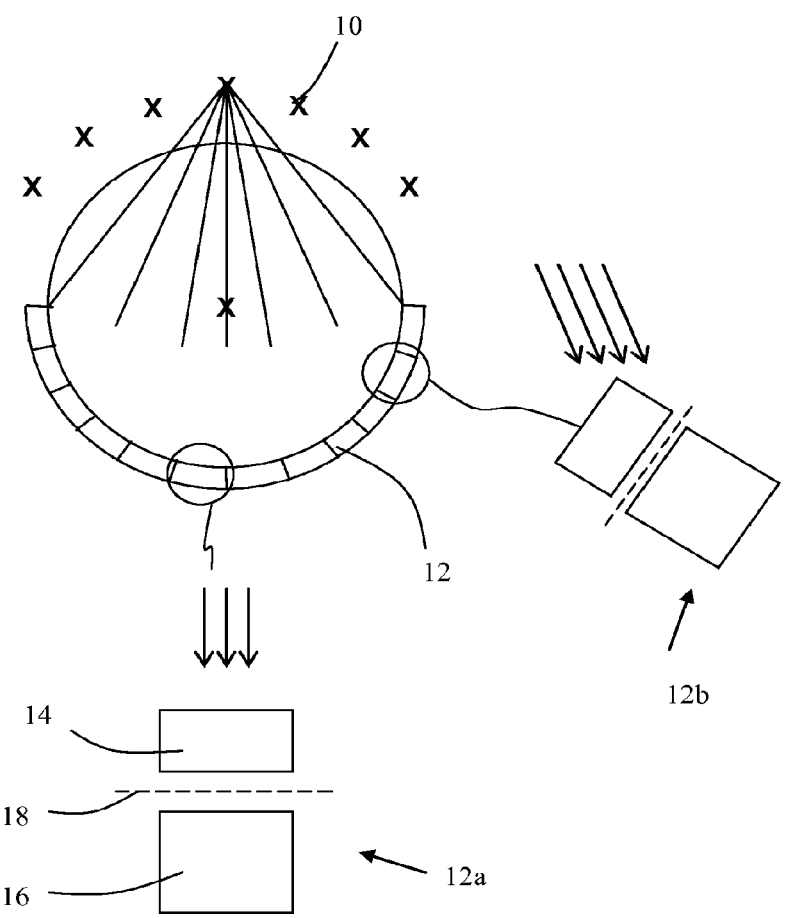
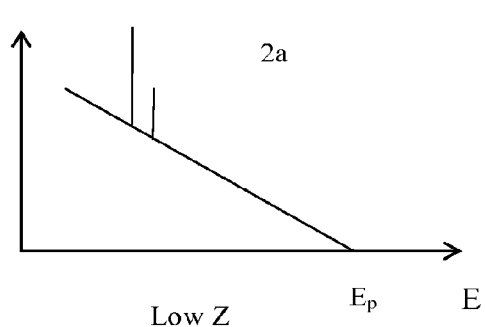
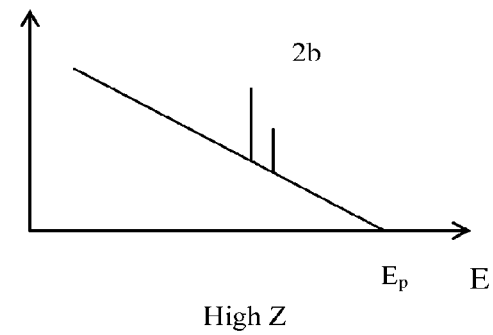
*Fig. 2*

*Fig. 6*
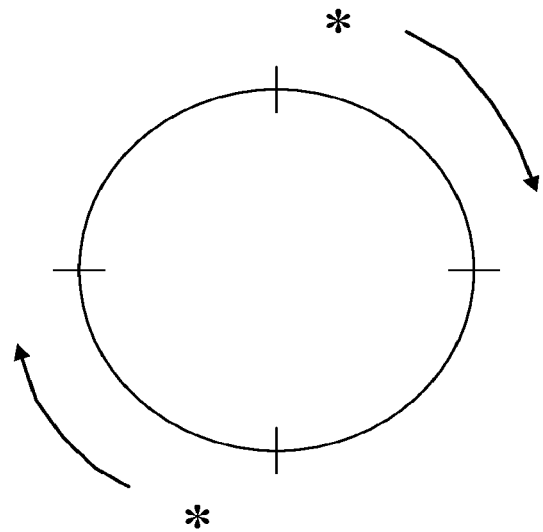
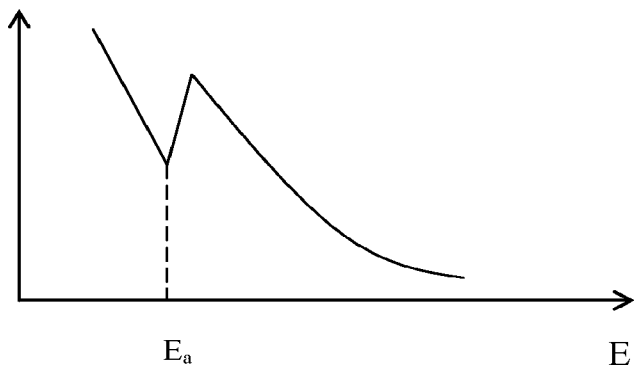
*Fig. 7*
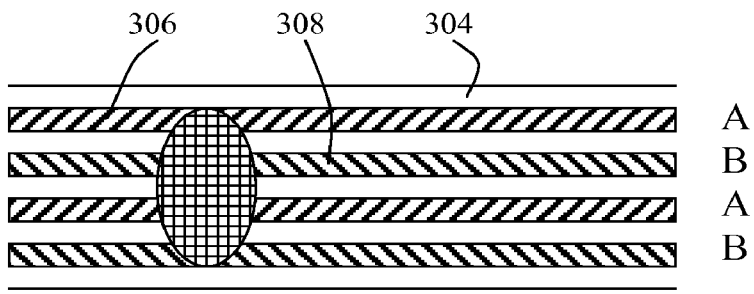
*Fig. 8*

X-RAY SCANNERS AND X-RAY SOURCES THEREFOR

CROSS-REFERENCE

The present invention is a continuation-in-part of U.S. patent application Ser. No. 12/097,422, filed on Jun. 13, 2008, which is a national stage application of PCT/GB06/04684, filed on Dec. 15, 2006, which relies on Great Britain Patent Application Number 0525593.0, filed on Dec. 16, 2005, for priority.

The present application also relies on Great Britain Patent Application No. 0904236.7, filed on Mar. 12, 2009, for priority.

All of the aforementioned applications are incorporated herein by reference.

FIELD OF THE INVENTION

The present invention relates to X-ray scanners and in particular to scanners arranged to use different energies of X-rays for use, for example, in the imaging or analysis of objects.

BACKGROUND

A new generation of multi-focus X-ray tubes are now being designed to address problems in imaging systems which involve rapid movement of the object under inspection. This is particularly important in tomographic imaging systems where object motion can create unacceptably high levels of artefact in reconstructed images. To address this problem, multi-focus X-ray sources are proposed in which often many hundreds of individual electron guns are arranged, typically into a circular array, and each electron gun is switched on sequentially to irradiate a respective point on a circular anode with the same radius as that of the electron guns. This forms a rotating X-ray source without the need for physical motion of the assembly, hence creating the opportunity for very high speed tomographic imaging.

In such tomographic X-ray systems, it is often desirable to provide materials discrimination capability which is typically achieved through the use of the reconstructed grey level of the tomographic image with calibration back to a set of known reference standards (e.g. air, water, aluminium).

It is recognised that further materials discrimination capability can be achieved when the energy spectrum of the X-ray beam is taken into account since each spectral component in the incident X-ray beam is attenuated to a different amount by each component material within the object under inspection. Low atomic number materials provide modest attenuation of low energy X-rays whilst high atomic number materials provide significant attenuation of low energy X-rays. By analysis of the X-ray spectrum after filtering by the object, it is possible to obtain further materials discrimination than if the X-ray spectrum is simply integrated.

In a practical X-ray system, it is expensive to measure the energy of every single X-ray photon that arrives at the detector. This is because the arrival rate of photons at each detector element is relatively high (often over 1 MHz photon arrival rate) and the complexity and associated power dissipation of the detection electronics becomes a significant issue.

One means to simplify the situation is to utilise more than one inexpensive integrating detector per imaging channel, but with a filter placed between one detector and the other. The filtered detector is generally made thick to measure the high energy components of the X-ray beam transmitted through the object. The unfiltered detector is usually quite thin and so responds preferentially to the low energy components of the transmitted X-ray beam.

SUMMARY OF THE INVENTION

The present invention provides an X-ray scanner comprising an electron source and an anode, the anode having a target surface with a series of material areas, which may be spaced along it in a scanning direction. The material areas may be formed from different materials. The electron source may be arranged to direct electrons at a series of target areas of the target surface, in a predetermined order, so as to generate X-ray beams having different energy spectra.

Each of the material areas may be formed of a uniform material, which may be a single element, such as a metal, or a mixture. The material areas may comprise strips which extend in a direction transverse to the scanning direction. Alternatively the material areas may comprise strips extending in a direction which is oblique to the scanning direction.

The material areas may be formed as thin films of target metals.

Each of the target areas, which may be defined by the focal area of the electron beam, may be within a respective one of the material areas. Alternatively each of the target areas may cover part of at least two of the material areas.

The scanner may further comprise a plurality of detectors arranged to detect the X-rays. The detectors may be substantially identical. The detectors may include two sets of detectors arranged to have different responses to X-rays of at least one energy, or to a predetermined range of energies. The detectors of one of the sets of detectors may include a filter material and a detector element. The detectors may be integrating detectors.

The scanner may further comprise processing means arranged to receive signals from the detectors, and to process the signals to generate an output. The output may be image data set arranged to generate an image.

The present invention further provides an X-ray scanner comprising an electron source and an anode, the anode having a target surface formed from a plurality of different materials. The electron source may be arranged to direct a beam of electrons at the target surface so as to generate, simultaneously, X-rays of two different energy spectra from the two materials. The scanner may further comprise two detector arrays having different response characteristics. For example one array may be more sensitive to X rays having one of the energy spectra, and the other array may be more sensitive to X-rays having the other of the energy spectra.

The detectors of one of the arrays of detectors may include a filter material and a detector element. The two materials may each be arranged to generate X-rays having intensity peak at a respective fluorescent energy. The filter material may be arranged to provide different attenuations at the two fluorescent energies. The filter material may have an absorption edge at a frequency between the two fluorescent energies.

The target surface may have a plurality of material areas each formed from one of the materials, and the electron source may be arranged to direct a beam of electrons at a target area of the target, the target area comprising part of at least two of the material areas.

The electron source may be arranged to direct electrons at a plurality of target areas spaced along the target. The material areas may be arranged as parallel strips each extending through a plurality of the target areas. The target surface may be formed from a mixture of the materials.

In one embodiment, the present invention is directed toward an X-ray scanner comprising an electron source and an anode, the anode having a target surface with a series of material areas spaced along it in a scanning direction, the material areas being formed from different materials, the electron source being arranged to direct electrons at a series of target areas of the target surface, in a predetermined order, so as to generate X-ray beams having different energy spectra.

Optionally, each of the material areas is formed of a uniform material. The material areas comprise strips which extend in a direction transverse to the scanning direction. The material areas comprise strips extending in a direction which is oblique to the scanning direction. The material areas are formed as thin films of target metals. Each of the target areas is within a respective one of the material areas. Each of the target areas covers part of at least two of the material areas.

Optionally, the system further comprises a plurality of detectors arranged to detect the X-rays. The detectors are substantially identical. The detectors include two sets of detectors arranged to have different responses to X-rays of at least one energy. One of the sets of detectors is more sensitive to X-rays over a first range of energies, and the other of the sets of detectors is more sensitive to X-rays over a second range of energies. The detectors of one of the sets of detectors includes a filter material and a detector element.

Optionally, the system further comprises processing means arranged to receive signals from the detectors, and to process the signals to generate an output. The output is image data set arranged to generate an image.

In another embodiment, the present invention is directed to an X-ray scanner comprising an electron source and an anode, the anode having a target surface formed from a plurality of different materials, the electron source being arranged to direct a beam of electrons at the target surface so as to generate, simultaneously, X-rays of two different energy spectra from the two materials, and two detector arrays having different response characteristics. The ratio of the responses of one of the detector arrays to X-rays having the two energy spectra of the two materials is different to the ratio of the responses of the other detector array to X-rays having those energy spectra. The detectors of one of the arrays of detectors include a filter material and a detector element. The two materials are each arranged to generate X-rays having intensity peak at a respective fluorescent energy, and the filter material is arranged to provide different attenuations at the two fluorescent energies. The filter material has an absorption edge at a frequency between the two fluorescent energies. The detectors of both the detector arrays include identical detector elements. The target surface has a plurality of material areas each formed from one of the materials, and the electron source is arranged to direct a beam of electrons at a target area of the target, the target area comprising part of at least two of the material areas. The electron source is arranged to direct electrons at a plurality of target areas spaced along the target. The material areas are arranged as parallel strips each extending through a plurality of the target areas. The target surface is formed from a mixture of the materials.

Preferred embodiments of the present invention will now be described by way of example only with reference to the accompanying drawings.

BRIEF DESCRIPTION OF THE DRAWINGS

FIG. 1 is schematic view of a known scanning system;
FIGS. 2*a* and 2*b* show graphs of X-ray energy spectra from different anode materials;
FIG. 6 is a schematic diagram showing operation of the system of FIG. 4;
FIG. 7 is a graph of X-ray absorption as a function of energy in a typical filter material;
FIG. 8 is front view of a target according to a second embodiment of the invention.

DETAILED DESCRIPTION

Figure 4:
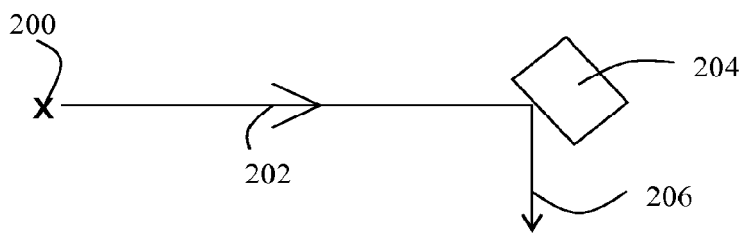
FIG. 4 is a schematic view of an X-ray source forming part of the scanning system of FIG. 3.

Referring to FIG. 1, an X-ray scanner comprises a ring array of X-ray sources 10, offset axially from a ring array of X-ray detectors 12. Each of the sources 10 is activated in turn and, for each source, the signals from the detectors 12 are stored and analysed. Each of the sensors is a known stacked sensor comprising a thin front detector element 14 in front of a thicker rear detector element 16, with a filter 18 between the two detector elements. The front detector element 14 is arranged to detect lower energy X-rays, the rear detector element 16 is arranged to detect higher energy X-rays, and the filter 18 is arranged to filter out the lower energy X-rays not absorbed by the front detector element 14.

Since all of the detectors are aligned with, and face, the axis X of the scanner, it will be seen that at the centre of the X-ray beam, a stacked detector 12*a* works well in that the front detector element 14, filter 18 and rear detector element 16 are all aligned with the direction of the incident X-ray beam. In contrast, at the edge of the beam in detector 12*b*, the front detector element 14, filter 18 and rear detector element 16 are not aligned with the beam and there is significant low energy leakage into the rear detector element 16. Similarly, the relatively large material thickness presented to the X-ray beam by the front detector element 14 causes high energy signal leakage into the measured signal. This signal leakage between detector elements compromises the ability of the X-ray system to provide materials discrimination.

Referring to FIG. 2, in one embodiment, the present invention provides energy discrimination by using different target materials in the X-ray source thereby modulating the spectral composition of the primary X-ray beam. FIG. 2 shows idealised X-ray spectra from an X-ray tube operating at the same tube voltage (with maximum X-ray energy Ep) but in FIG. 2*a* with a low atomic number (Z) anode (such as silver, Ag) and in FIG. 2*b* a high atomic number anode (such as tungsten, W). It is seen that the Bremsstrahlung spectral components are similar in each case, but the characteristic fluorescence lines, which form peaks of high intensity in the energy spectrum, are quite different in energy. The relative position of the fluorescence radiation results in a significantly higher mean spectral energy for the tungsten target than that observed with the silver target. When integrating the transmitted X-ray signal after attenuation by a complex object, the silver anode X-ray beam will be significantly attenuated by high atomic number materials whereas the tungsten spectrum will be less highly attenuated. Taking the ratio of the tungsten to silver anode X-ray data provides an equivalent set of data as is obtained when using two detector sets.

Figure 3:
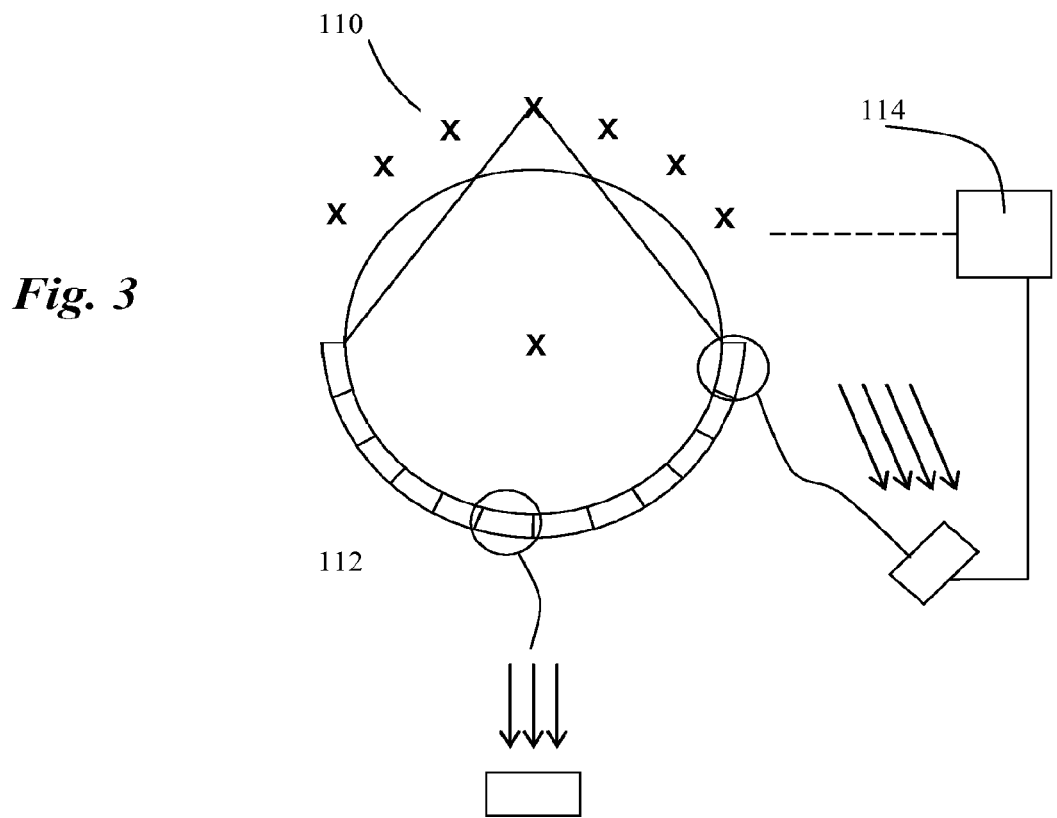
FIG. 3 is a schematic view of a scanning system according to an embodiment of the invention.

Referring to FIG. 3, an X-ray scanner according to an embodiment of the invention, comprises an array of X-ray sources 110 and an array of X-ray detectors 112 axially offset from the sources. In each case the array is spaced around the axis of the scanner. Each of the sources is arranged to direct beams of electrons towards the axis of the scanner. Each of the detectors is also directed towards the axis of the scanner. In this case each array is a ring array, but either the sources or the detectors may form a partial ring array, or other shaped arrays. However it is desirable that the sources, or the source positions within the sources from which the X-ray beams are generated, are arranged in a common plane perpendicular to the scanner axis. Similarly the detectors are arranged in one or more arrays each in a plane perpendicular to the scanner axis. A control system 114 is arranged to control the sources 110 so that each of them can be activated independently to scan an object in the scanner. Again, the sources 110 are arranged to be activated in turn, but in this case the sources 110 are arranged to generate X-rays with different energy spectra, and the detectors are single element non-stacked detectors. The detectors are all the same, having the same response, i.e. producing the same output in response to X-rays over a range of energies. In this case the detectors are integrating detectors which detect X-rays over a range of energies. They produce an output which varies with the total X-ray intensity over that range. The signal leakage between detectors 112 has been eliminated since the small amount of filtering by adjacent detectors at the edge of the active beam can be taken into account by straightforward calibration factors.

Referring to FIG. 4 the X-ray source ring is made up of a number of X-ray tubes, each comprising an electron source 200 arranged to produce a beam 202 of electrons, and an anode 204. The electron source 200 is controllable in known manner to scan the electron beam 202 longitudinally along the anode 204 to generate X-rays 206 from source positions along the anode 204.

Figure 5:
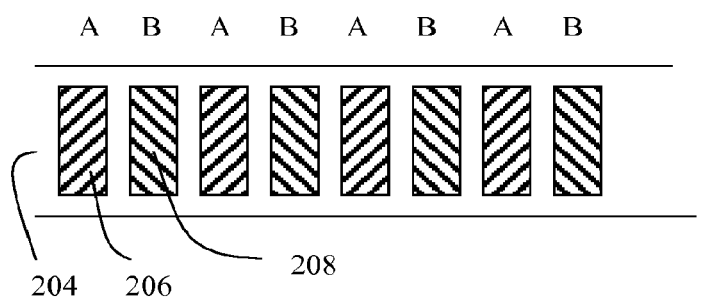
FIG. 5 is a front view of an anode forming part of the system of FIG. 4.

Referring to FIG. 5, the anode 204 is coated with thin film areas of two different target materials A and B. Here, target material A is patterned onto the anode 204 in rectangular areas or blocks 206, each block being of uniform composition over its own area, in this case being of a single element, and larger than the focal region of the incident electron beam. Interspersed between each target block 206 of material A is a target block 208 which comprises a different target material B. The target material blocks 206, 208 therefore form a linear array of target areas or positions, arranged in a ring around the scanner, with the target material alternating between the two different materials A and B along the array.

Referring to FIG. 6, the scanner can be controlled so that two electron beams are swept around the object under inspection, the two beams being preferably offset by 180 degrees plus the angular displacement between an adjacent pair of A and B type target blocks. In this embodiment the scanning is performed using a switchable electron source which is controlled to switch on an electron beam directed at one of the target areas and then switching it off again, and then switching electron beams directed at each of the other target positions on and off in turn, so that the beam is swept across the target positions in steps. This results in one block of material A and one of material B being targeted simultaneously, the two active target areas being almost opposite each other so that half of the detector array 112 can be used to detect X rays from one of them, and the other half of the detector array 112 to detect X rays simultaneously from the other. Typically, the spacing of the blocks 206 of materials A and B is selected such that the angular sampling rate of both trajectories meets the Nyquist sampling criteria.

The data from the detectors 112 may then be used to reconstruct independent tomographic images, one for each source type A or B, which can then be subtracted one from the other or otherwise analysed following image reconstruction. Alternatively, the projection data can be combined prior to backprojection to form a modified projection data set.

Referring to FIG. 7, a further embodiment of the invention is the same as the first embodiment but uses filters associated with the detectors so as to vary the response characteristics of the detectors, i.e. the magnitude of their response as a function of X-ray energy, to provide further energy discrimination. To provide discrimination the response characteristics need to of a different shape, i.e. varying differently with energy, not just of a different scale. FIG. 7 shows the absorption coefficient µ of a typical filter material as a function of X-ray energy. It can be seen that the absorbing material has an absorption edge at a characteristic energy Ea, this energy being equal to that at which participation of K-shell atomic electrons becomes possible. This results in low absorption at energies just below the characteristic energy Ea and high absorption at energies just above the characteristic energy Ea. This allows the filter material to be used to block some X-ray energies and pass other X-ray energies. By selecting carefully matched target materials with different fluorescent peaks and an appropriate filter material, it is possible to further enhance the selective energy response of the integrating detectors. For example, with suitable filtering, one set of detectors can be made more sensitive than the other to X-rays at the fluorescent peak of one of the target materials, or over a first range of energies which may include that peak, and the other set of detectors can be made more sensitive than the first to X-rays at the fluorescent peak of the other target material, or over a second range of energies which can include that peak. More generally, the ratio of the responses of one of the detector arrays to X-rays at the two fluorescent peak energies is different to the ratio of the responses of the other. Similarly the ratio of the responses of one of the detector arrays to X-rays having the two energy spectra of the two materials is different to the ratio of the responses of the other detector array to X-rays having those energy spectra. As an example, a Tantalum filter strongly absorbs Tungsten characteristic X-rays but is relatively transparent to Molybdenum characteristic X-rays.

Figure 9:
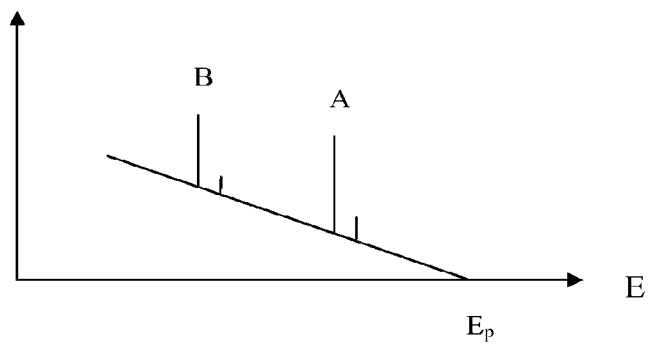
FIG. 9 is graph showing the energy spectrum of X-rays produced from the target of FIG. 8.

Referring to FIG. 8, in another embodiment which includes a detector arrangement as in FIG. 7, the target area of the anode 304 has parallel strips 306, 308 of target metal A and B formed on it, extending in the direction S in which the electron beam is scanned, and the electron beam is designed to be large enough to irradiate both target metals A and B simultaneously. In this case there are four strips, two of each material A and B, but obviously other numbers of strips can be used. A composite X-ray spectrum is generated having an energy spectrum as that shown in FIG. 9 which is the sum of the spectra of the two materials A and B having two peaks each produced by one of the target materials A and B. By placing a suitable filter material at some of the detectors, for example as in FIG. 7, it is possible to generate different responses, with different energy dependence, at different detectors.

Figure 10:
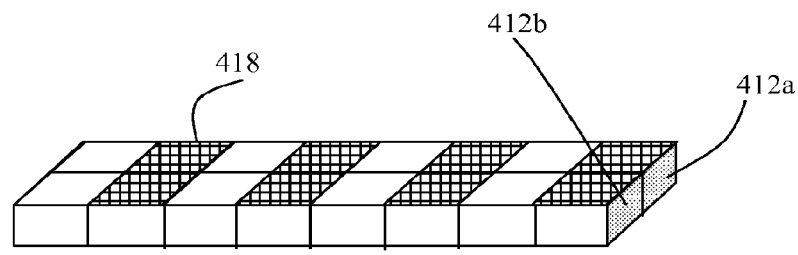
FIG. 10 is sketch of part of a detector array for use with the target of FIG. 8.
Figure 11:
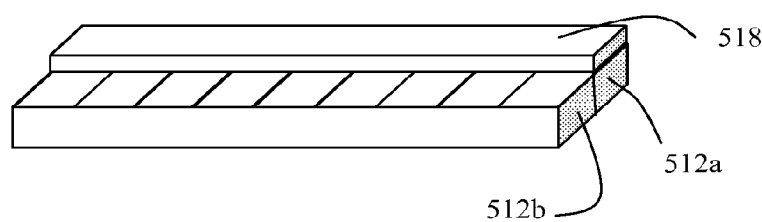
FIG. 11 is a sketch of part of a further detector array for use with the target of FIG. 8.

Referring to FIG. 10, in one embodiment a two-ring detector array comprises first and second adjacent rings 412a, 412b of detectors, with individual metal filters 418 placed on every other detector in each ring. Referring to FIG. 11, in another embodiment a two ring detector array 512 is used in which a strip of filter material 518 is placed over the whole of one ring 512a and no filter is used on the other ring 512b. Similar patterns may be used on multi-ring detector systems as appropriate. Both of these detector arrangements can be used with the targets of FIG. 5 or FIG. 8.

Figure 12:
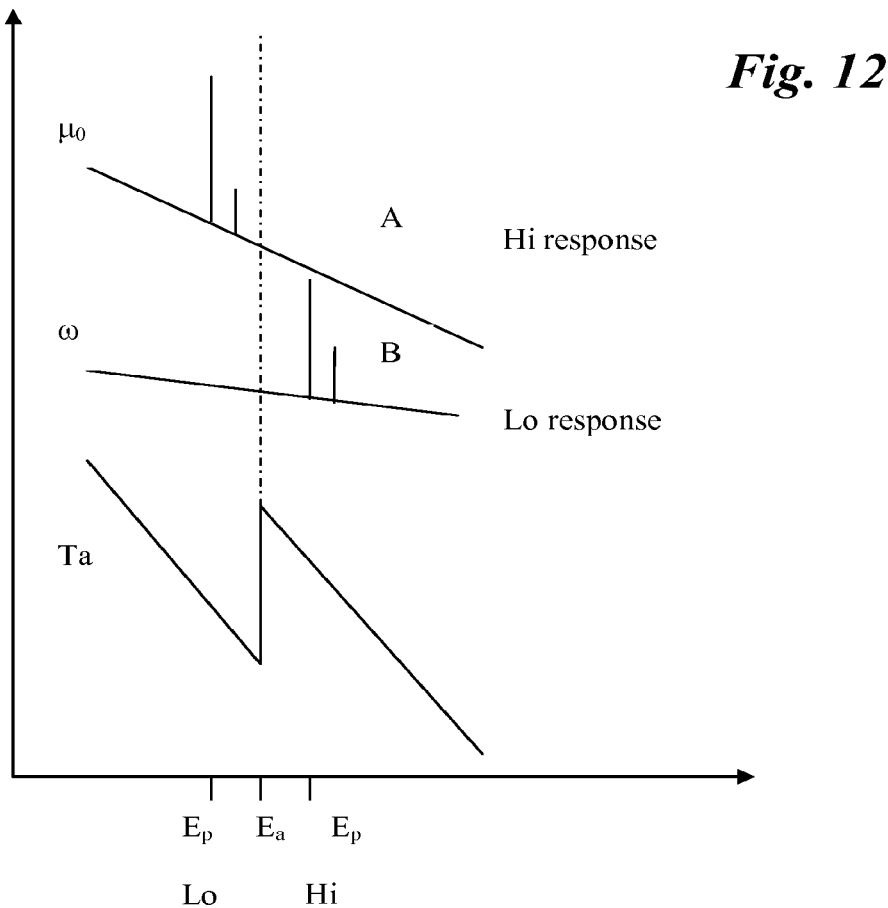
FIG. 12 is a graph showing the matching of the filters of FIGS. 10 and 11 with the target of FIG. 8.

Referring to FIG. 12, in either detector arrangement, the filter material is chosen so that absorption edge Ea falls at an energy between the two peaks in the composite X-ray spectrum. As described above, if Mo and W are used as the two target materials, then Ta can be used as a suitable filter material.

It will be appreciated that the combination of two target materials with different X-ray energy spectra having different peaks, and a suitably selected filter, provides quasi monoenergetic imaging for improved accuracy materials analysis, as it provides a high degree of differentiation between the outputs from the two sets of detectors, which is highly dependent on the absorption spectrum of the object being scanned, and therefore provides a good degree of, for example, discrimination between objects of different materials.

Complex targets can be made through the use of sputter coating. Using multiple sputter targets and shadow or other masking technologies, it is straightforward to pattern any of the target configurations. To ensure good adhesion between the target metal A, B and the segmented anode base metal, it is possible to either alloy or diffuse the target metal into the anode base. Typically this alloying or diffusion process is conducted in a vacuum or hydrogen filled furnace operating at suitably high temperatures (typically in the range 500-1000° C.). Depending on the process conditions chosen, a thin interface layer can be formed or the entire target metal can be alloyed into the base metal.

As a further refinement of this process, a multi-layer target can be formed using, for example, sputter coating of thin films (10-100 angstrom for example) of various different coating metals (tungsten and uranium, for example) one on top of another. The multi-layer target can then be alloyed/diffused together and into the base metal in order to form a target that produces reasonably complex X-ray spectra during electron bombardment.

Figure 13:
FIG. 13 is a front view of a target according to a third embodiment of the invention.

Referring to FIG. 13, in a further embodiment the two target materials A and B of different atomic number Z are again arranged in alternate areas or strips along the anode, but in this case the strips of target material are arranged at an oblique angle, in this case about 45°, to the direction of scanning S of the electron beam. The strips are narrow enough, and angled such that the offset between their upper and lower ends, in the direction of scanning of the electron beam, is at least equal to their width. This means that the electron beam, that is large enough to extend across substantially the full width of the target area, and as wide in the scanning direction as the strips, will always cover an area of the target that is made up of approximately equal areas of the two target materials. This allows a detector array similar to that of FIG. 10 or FIG. 11 to be used.

Figure 14:
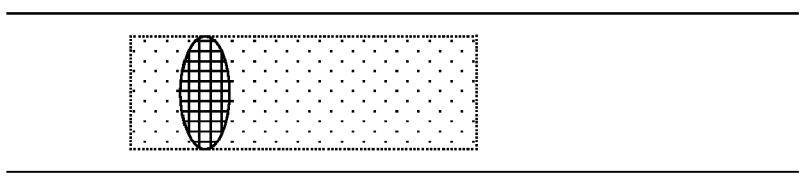
FIG. 14 is a front view of a target according to a fourth embodiment of the invention.

Referring to FIG. 14, in a further embodiment the target area of the anode is covered with a mixture of two target materials A and B with different atomic number. This again means that the X-ray beam generated has as spectrum with two peaks in it, which can be separated by filtering for detection, for example using the detector arrangements of FIG. 11 or FIG. 12.

It will be appreciated that, in embodiments described in which two target materials are used, it would be possible in some circumstances to use three or more target materials to obtain further energy discrimination.

The invention claimed is:

1. An X-ray scanner comprising
a first electron source configured to generate a first electron beam; and
an anode having a target surface comprising a first material and a second material, wherein
said first material is different from said second material,
said first material and second material form a pattern on said target surface, the pattern comprising an elongated strip of the first material alternating with an elongated strip of the second material to form an array of alternating target areas in a ring around said scanner,
the first electron source is configured to irradiate a strip of both the first material and second material simultaneously.

2. The X-ray scanner of claim 1 wherein the first and second material are formed of a uniform material.

3. The X-ray scanner of claim 1 wherein, upon irradiating the strip of both the first material and second material simultaneously, a composite X-ray spectrum is generated having an energy spectrum that is a sum of a spectra of the first material and a spectra of the second material.

4. The X-ray scanner of claim 1 further comprising a second electron source configured to generate a second electron beam.

5. The X-ray scanner of claim 1 wherein the first material area comprises a strip that extends in a direction parallel to the scanning direction.

6. The X-ray scanner of claim 1 wherein the second material area comprises a strip that extends in a direction parallel to the scanning direction.

7. The X-ray scanner of claim 1 wherein the first material area comprises a strip that extends in a direction which is oblique to the scanning direction.

8. The X-ray scanner of claim 1 wherein the second material area comprises a strip that extends in a direction which is oblique to the scanning direction.

9. The X-ray scanner of claim 1 wherein the first material area comprises a strip that extends in a direction which is transverse to the scanning direction.

10. The X-ray scanner of claim 1 wherein the second material area comprises a strip that extends in a direction which is transverse to the scanning direction.

11. The X-ray scanner of claim 1 wherein the first or second material area comprises a thin film of metal.

12. The X-ray scanner of claim 1 further comprising detectors, wherein the detectors comprise a first set of detectors and a second set of detectors and wherein, relative to said second set of detectors, the first set of detectors is more sensitive to X-rays over a spectra generated from irradiating the first material, and, relative to said first set of detectors, the second set of detectors is more sensitive to X-rays over a spectra generated from irradiating the second material.

13. The X-ray scanner of claim 12 wherein the second set of detectors comprises a filter material and a detector element.

14. The X-ray scanner of claim 1 further comprising detectors, wherein the detectors comprise a first set of detectors and a second set of detectors and wherein said first set of detectors has a different response characteristic from said second set of detectors and wherein the first set of detectors is configured to receive X-rays of a first energy spectra and the second set of detectors is configured to receive X-rays of a second energy spectra.

15. The X-ray scanner of claim 1 wherein the first and second materials are each arranged to generate X-rays having an intensity peak at two different respective fluorescent energies, and a filter material is arranged to provide different attenuations at the two fluorescent energies.

16. The X-ray scanner of claim 15 wherein the filter material has an absorption edge at a frequency between the two fluorescent energies.

17. A method of generating X-rays comprising
providing at least one electron source;
providing an anode with a target surface formed with parallel, elongated, alternating sections of at least two different material areas spaced along the target surface in a scanning direction; and
directing an electron beam from the at least one electron source to simultaneously irradiate both of said at least two different material areas to generate an X-ray beam of at least two different energy spectra.

18. The method of generating X-rays of claim 17 further comprising detecting radiation using a first set of detectors and a second set of detectors and wherein said first set of detectors has a different response characteristic from said second set of detectors and wherein the first set of detectors is configured to receive X-rays of a first energy spectra and the second set of detectors is configured to receive X-rays of a second energy spectra.

19. The method of generating X-rays of claim 17 further comprising detecting radiation using a first set of detectors and a second set of detectors and wherein, relative to said second set of detectors, the first set of detectors is more sensitive to X-rays over a spectra generated from irradiating a first of the at least two different material areas, and, relative to said first set of detectors, the second set of detectors is more sensitive to X-rays over a spectra generated from irradiating a second of the at least two different material areas.

* * * * *